US012673179B2

(12) United States Patent
Yang et al.

(10) Patent No.: US 12,673,179 B2
(45) Date of Patent: Jul. 7, 2026

(54) REHABILITATION ASSISTANT SYSTEM FOR PATIENTS WITH DEPRESSION

(71) Applicants: Asia University, Taichung City (TW); METABRAIN TECHNOLOGY PTE. LTD., Singapore (SG)

(72) Inventors: Shang-Yu Yang, Taichung City (TW); Shin-Da Lee, Taichung (TW); Kuan-Pin Su, Taichung (TW); Chen-Chao Hsu, Taichung City (TW)

(73) Assignees: METABRAIN TECHNOLOGY PTE. LTD., Singapore (SG); ASIA UNIVERSITY, Taichung City (TW)

( * ) Notice: Subject to any disclaimer, the term of this patent is extended or adjusted under 35 U.S.C. 154(b) by 986 days.

(21) Appl. No.: 17/896,675

(22) Filed: Aug. 26, 2022

(65) Prior Publication Data

US 2023/0066359 A1 Mar. 2, 2023

(30) Foreign Application Priority Data

Aug. 27, 2021 (TW) ................................. 110131806

(51) Int. Cl.
*A61M 21/02* (2006.01)
*A61M 21/00* (2006.01)
(Continued)

(52) U.S. Cl.
CPC ......... *A61M 21/02* (2013.01); *A61N 1/36025* (2013.01); *A61N 2/002* (2013.01); *A61N 5/0619* (2013.01); *A63B 22/0605* (2013.01); *A61M 2021/0027* (2013.01); *A61M 2021/0044* (2013.01); *A61M 2021/005* (2013.01);
(Continued)

(58) Field of Classification Search
CPC .................. A61M 21/00; A61M 21/02; A61M 2021/0005; A61M 2021/0022; A61M 2021/0027; A61M 2021/0044; A61M 2021/005; A61M 2021/0055; A61M 2021/0072; A61N 1/36025; A61N 2/002; A61N 2/004; A61N 2/006; A61N 2/008;
(Continued)

(56) References Cited

U.S. PATENT DOCUMENTS

2016/0270656 A1* 9/2016 Samec ................... A61B 5/398

* cited by examiner

*Primary Examiner* — Carrie R Dorna
(74) *Attorney, Agent, or Firm* — MUNCY, GEISSLER, OLDS & LOWE, P.C.

(57) ABSTRACT

A rehabilitation assistant system for a patient with depression is provided, comprising a support unit, an audio stimulation unit, an acupoint stimulation unit, an electronic stimulation unit, a display and optical frequency-flashed stimulation and an exercise unit. The audio stimulation unit comprises two speakers configured for broadcasting a binaural beats with frequency following response which has an audio frequency difference to two ears of the user. The acupoint stimulation unit comprises acupoint agents, and at least a part of the acupoint agents are arranged on the support unit. The electronic stimulation unit comprises two electrical stimulation agents arranged on the support unit, and the display and optical frequency-flashed stimulation is arranged on the support unit and is switchable between a display mode and an optical frequency-flashed stimulation mode so that multiple stimulations are performed simultaneously in a single treatment course.

15 Claims, 11 Drawing Sheets
(4 of 11 Drawing Sheet(s) Filed in Color)

(51) Int. Cl.
| | |
|---|---|
| *A61N 1/36* | (2006.01) |
| *A61N 2/00* | (2006.01) |
| *A61N 5/06* | (2006.01) |
| *A63B 22/06* | (2006.01) |

(52) U.S. Cl.
CPC .............. *A61M 2021/0055* (2013.01); *A61M 2205/3553* (2013.01); *A61M 2230/04* (2013.01); *A61N 2005/0645* (2013.01); *A61N 2005/0647* (2013.01)

(58) Field of Classification Search
CPC ........ A61N 2/02; A61N 5/0619; A61H 39/00; A61H 2039/005
See application file for complete search history.

Center for Epidemiologic Studies Depression Scale (CES-D), NIMH

Below is a list of the ways you might have felt or behaved. Please tell me how often you have felt this way during the past week.

| | During the Past Week | | | |
|---|---|---|---|---|
| | Rarely or none of the time (less than 1 day) | Some or a little of the time (1-2 days) | Occasionally or a moderate amount of time (3-4 days) | Most or all of the time (5-7 days) |
| 1. I was bothered by things that usually don't bother me. | ☐ | ☐ | ☐ | ☐ |
| 2. I did not feel like eating; my appetite was poor. | ☐ | ☐ | ☐ | ☐ |
| 3. I felt that I could not shake off the blues even with help from my family or friends. | ☐ | ☐ | ☐ | ☐ |
| 4. I felt I was just as good as other people. | ☐ | ☐ | ☐ | ☐ |
| 5. I had trouble keeping my mind on what I was doing. | ☐ | ☐ | ☐ | ☐ |
| 6. I felt depressed. | ☐ | ☐ | ☐ | ☐ |
| 7. I felt that everything I did was an effort. | ☐ | ☐ | ☐ | ☐ |
| 8. I felt hopeful about the future. | ☐ | ☐ | ☐ | ☐ |
| 9. I thought my life had been a failure. | ☐ | ☐ | ☐ | ☐ |
| 10. I felt fearful. | ☐ | ☐ | ☐ | ☐ |
| 11. My sleep was restless. | ☐ | ☐ | ☐ | ☐ |
| 12. I was happy. | ☐ | ☐ | ☐ | ☐ |
| 13. I talked less than usual. | ☐ | ☐ | ☐ | ☐ |
| 14. I felt lonely. | ☐ | ☐ | ☐ | ☐ |
| 15. People were unfriendly. | ☐ | ☐ | ☐ | ☐ |
| 16. I enjoyed life. | ☐ | ☐ | ☐ | ☐ |
| 17. I had crying spells. | ☐ | ☐ | ☐ | ☐ |
| 18. I felt sad. | ☐ | ☐ | ☐ | ☐ |
| 19. I felt that people dislike me. | ☐ | ☐ | ☐ | ☐ |
| 20. I could not get "going." | ☐ | ☐ | ☐ | ☐ |

SCORING: zero for answers in the first column, 1 for answers in the second column, 2 for answers in the third column, 3 for answers in the fourth column. The scoring of positive items is reversed. Possible range of scores is zero to 60, with the higher scores indicating the presence of more symptomatology.

FIG. 7

REHABILITATION ASSISTANT SYSTEM FOR PATIENTS WITH DEPRESSION

BACKGROUND OF THE INVENTION

Field of the Invention

The present invention relates to a rehabilitation assistant system, in particular to a rehabilitation assistant system for a patient with depression.

Description of the Prior Art

Depression is a kind of mental disease. Its treatment can be mainly divided into psychological treatment and drug treatment. The patients with serious depression may also have a tendency of committing suicide, resulting in increased social costs. Therefore, the study of depression and other mitigation methods is still ongoing.

SUMMARY OF THE INVENTION

Accordingly, it is an object of the present invention to provide a rehabilitation assistant system for a patient with depression.

Accordingly, the rehabilitation assistant system for the patient with depression of the present invention, for use by a user, comprises a support unit, an audio stimulation unit, an acupoint stimulation unit, an electronic stimulation unit, a display and optical frequency-flashed stimulation, an exercise unit, and a control unit.

The support unit corresponds to a head shape of the user and comprises two ear portions corresponding to both ears of the user, a top side portion connected between the ear portions and upwardly crossing over the top of the head of the user, a rear side portion connected between the ear portions and rearwardly crossing over the rear skull of the user, and a front side portion connected between the ear portions and forwardly crossing over the user. The audio stimulation unit comprises two speakers arranged at the ear portions, the speakers being used for broadcasting the binaural beats with frequency following response to two ears of the user, the binaural beats with frequency following response having an audio frequency difference. The acupoint stimulation unit comprises several acupoint agents, wherein at least a part of the acupoint agents are arranged on the support unit, the acupoint agents being used to output a laser light for physical stimulation of the user's acupoint; one of the acupoint agents is arranged at the center of the top side portion in an adjustable position so as to correspond to the Baihui acupoint of the user; one of the acupoint agents is arranged at the front side portion in an adjustable position and located forwardly at a distance of ten times the finger distance from the center of the top side portion so as to correspond to the Yintang acupoint of the user, the finger distance being substantially 2.3 centimeters. The electronic stimulation unit comprises two electrical stimulation agents arranged on the support unit, wherein the electrical stimulation agents are used for outputting a current to the head of the user to perform transcranial electrical stimulation and outputting an electromagnetic pulse to perform physical stimulation of one of the transcranial magnetic stimulation. The display and optical frequency-flashed stimulation is arranged on the support unit and can switch between a display mode and an optical frequency-flashed stimulation mode, wherein the display and optical frequency-flashed mode displays a virtual image for viewing by the two eyes of the user when in the display mode; the display and optical frequency-flashed stimulation stimulates the two eyes of the user with a flashing picture when in the optical frequency-flashed stimulation mode. The exercise unit is configured for being operated by the user to take exercise. The control unit is electrically connected to the speakers, the acupoint agents, the electrical stimulation agents, the display and optical frequency-flashed stimulation and the exercise unit, stores digital information about the binaural beats with frequency following response, and can simultaneously control the speakers to broadcast the binaural beats with frequency following response, the acupoint agents to emit physical stimulation, the electrical stimulation agents to emit physical stimulation, and the display and optical frequency-flashed stimulation to switch between the display mode and the optical frequency-flashed stimulation mode.

The effect of the present invention is as follows. By providing the speakers, the acupoint agents and the electrical stimulation agents, the display and optical frequency-flashed stimulation and the exercise unit, the user can simultaneously obtain multiple stimulation in a single treatment course, so as to improve the rehabilitation efficiency of the patient with depression.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other features and effects of the invention will be apparent from the embodiments with reference to the drawings, in which:

FIG. 7 is a current evaluation table;

DETAILED DESCRIPTION OF THE PREFERRED EMBODIMENTS

Figure 1:
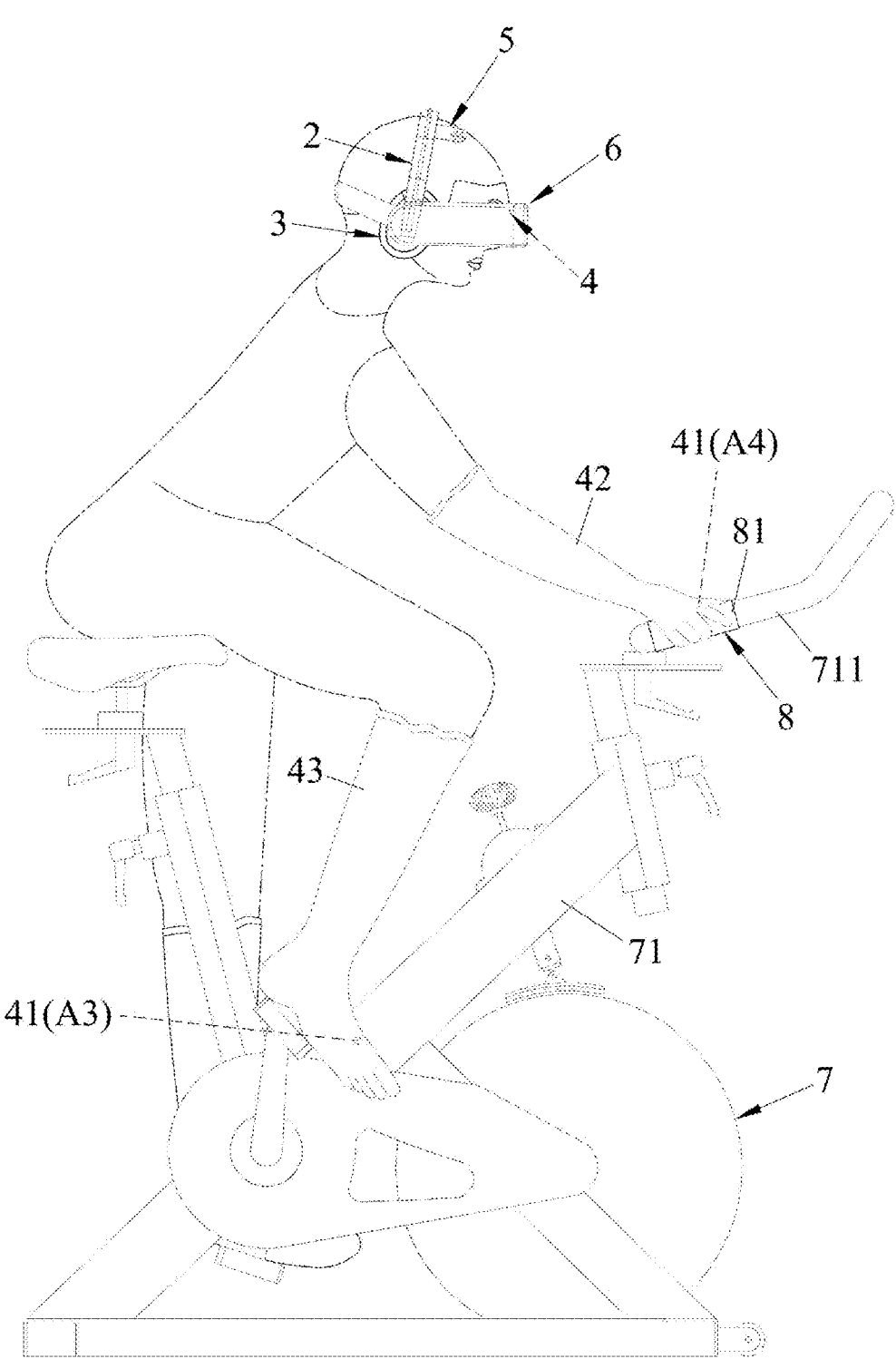
FIG. 1 is a schematic view of an embodiment of a rehabilitation assistant system for a patient with depression according to the present invention.
Figure 2:
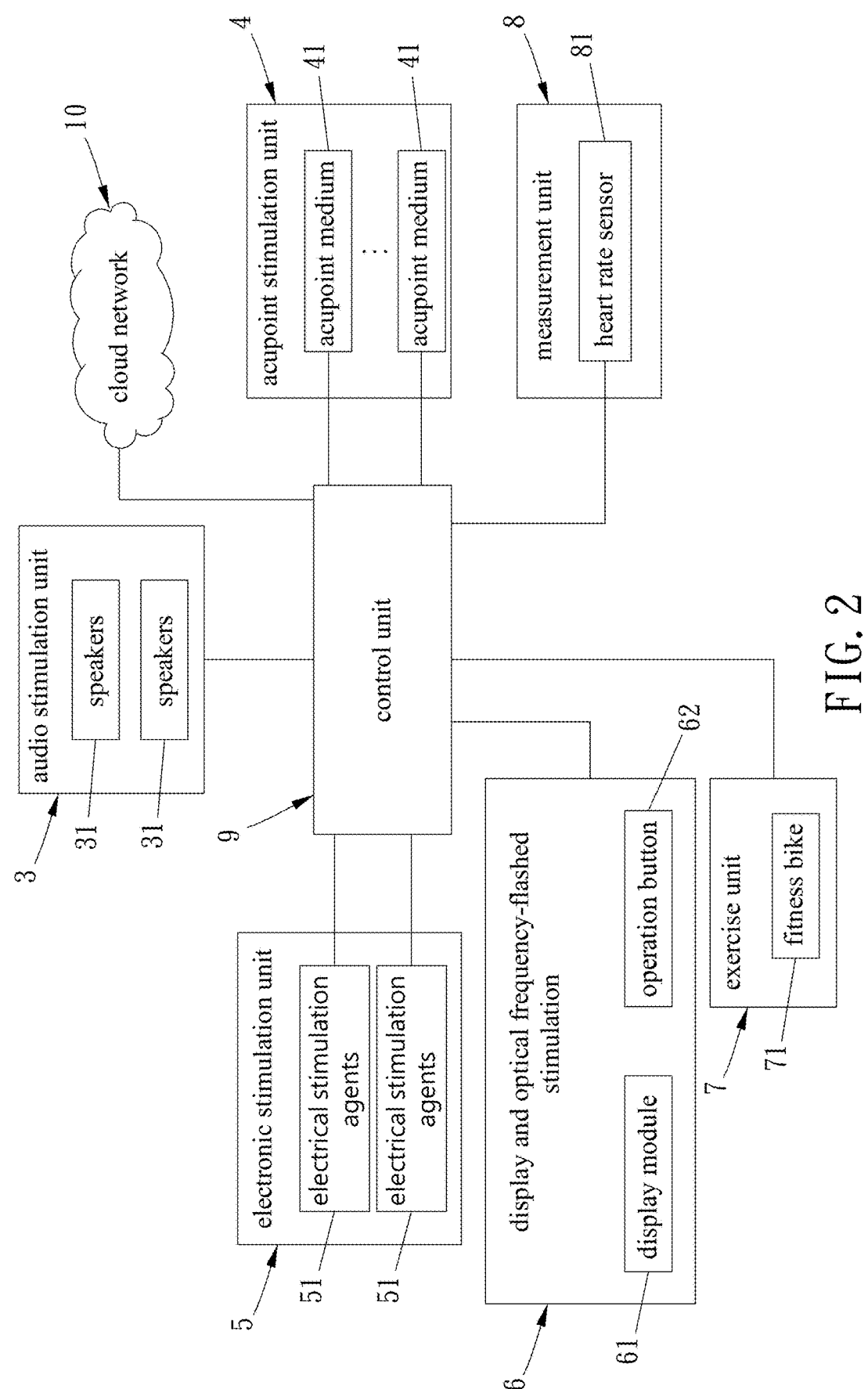
FIG. 2 is an electrical block diagram of the embodiment.
Figure 3:
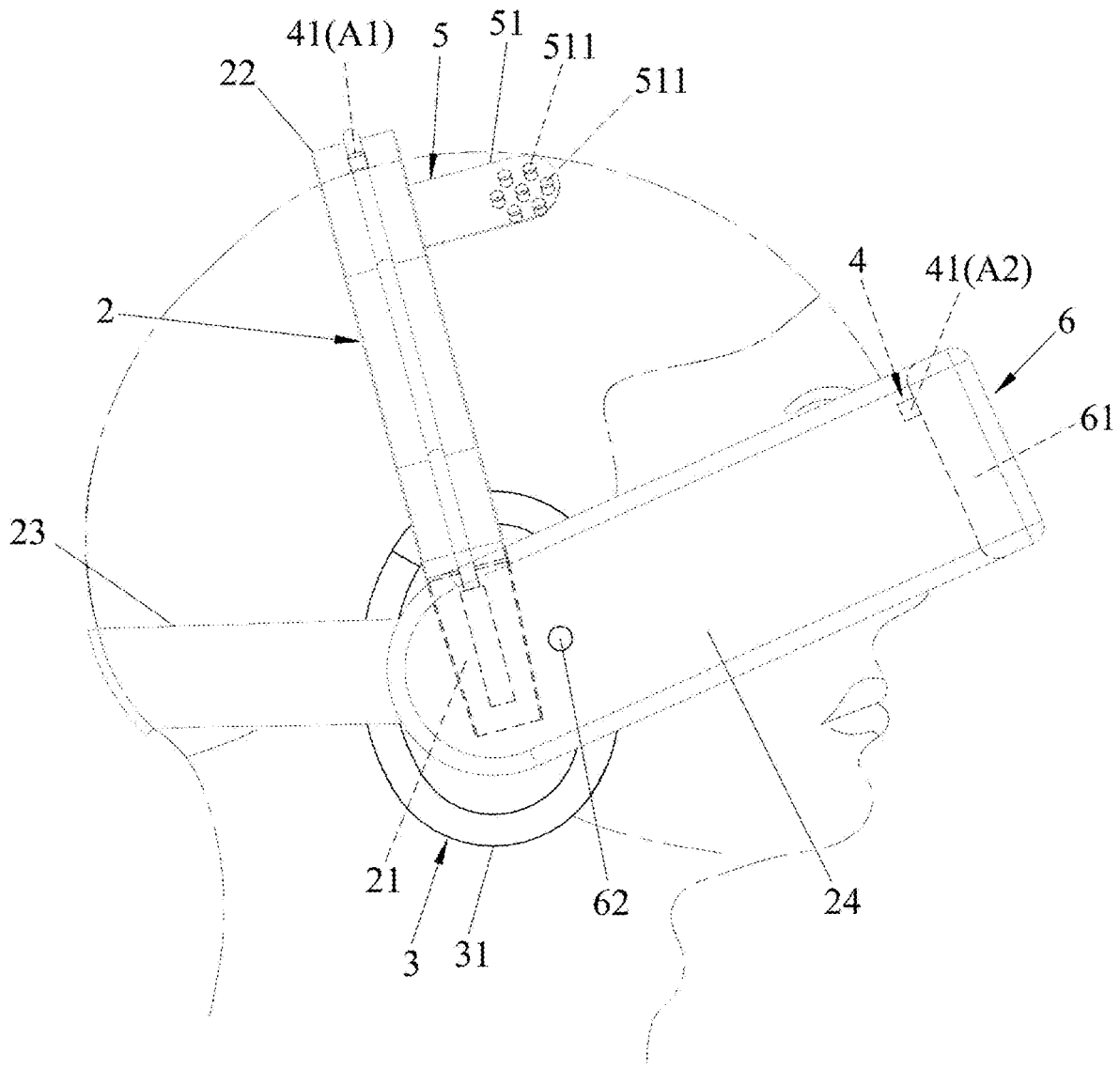
FIG. 3 is a fragmentary side view of the embodiment.

Referring to FIGS. 1, 2 and 3, an embodiment of a rehabilitation assistant system for a patient with depression of the present invention, for use by a user, includes a support unit 2, an audio stimulation unit 3, an acupoint stimulation unit 4, an electronic stimulation unit 5, a display and optical frequency-flashed stimulation 6, an exercise unit 7, a measurement unit 8, and a control unit 9.

Figure 4:
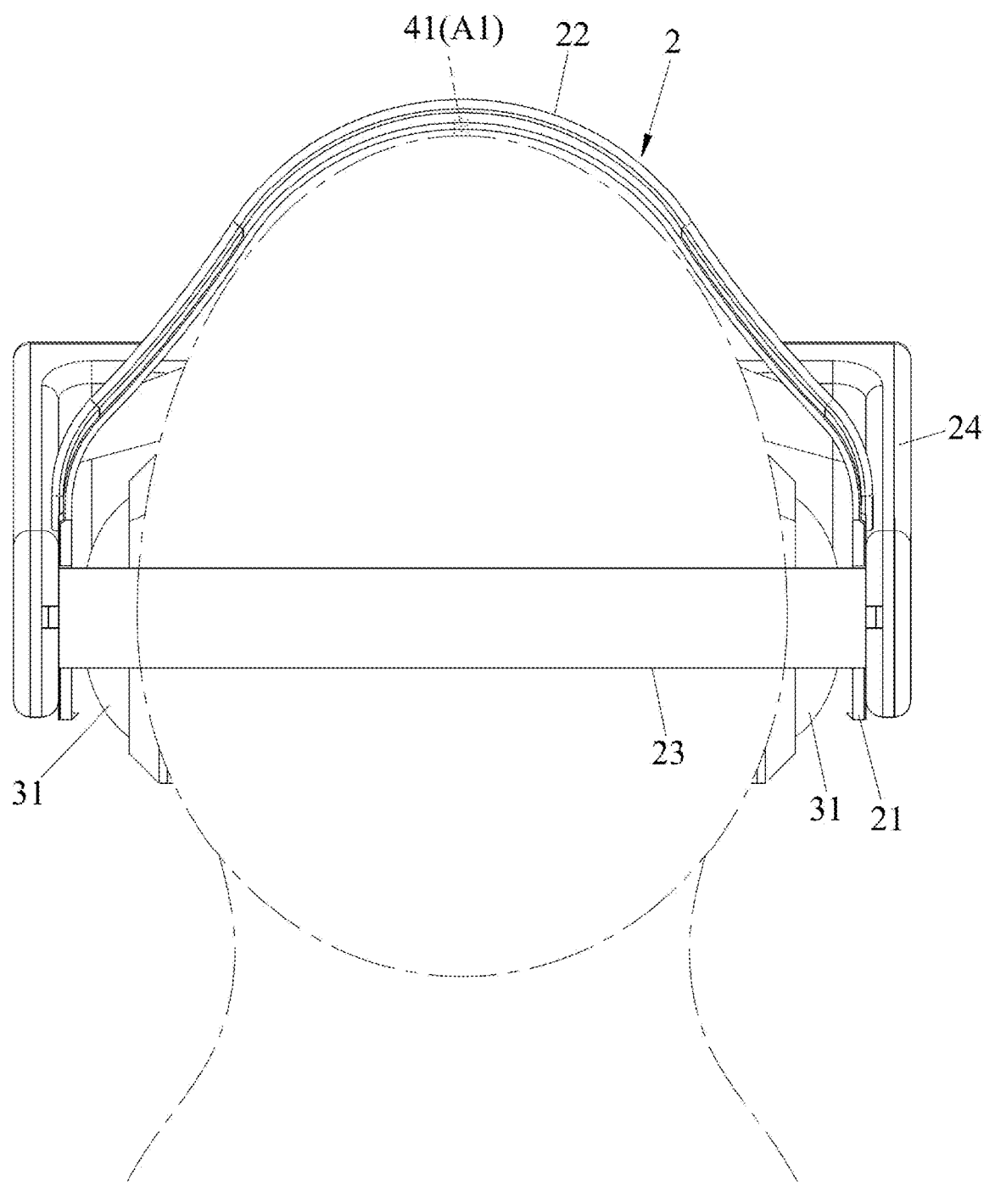
FIG. 4 is a fragmentary rear view of the embodiment.
Figure 5:
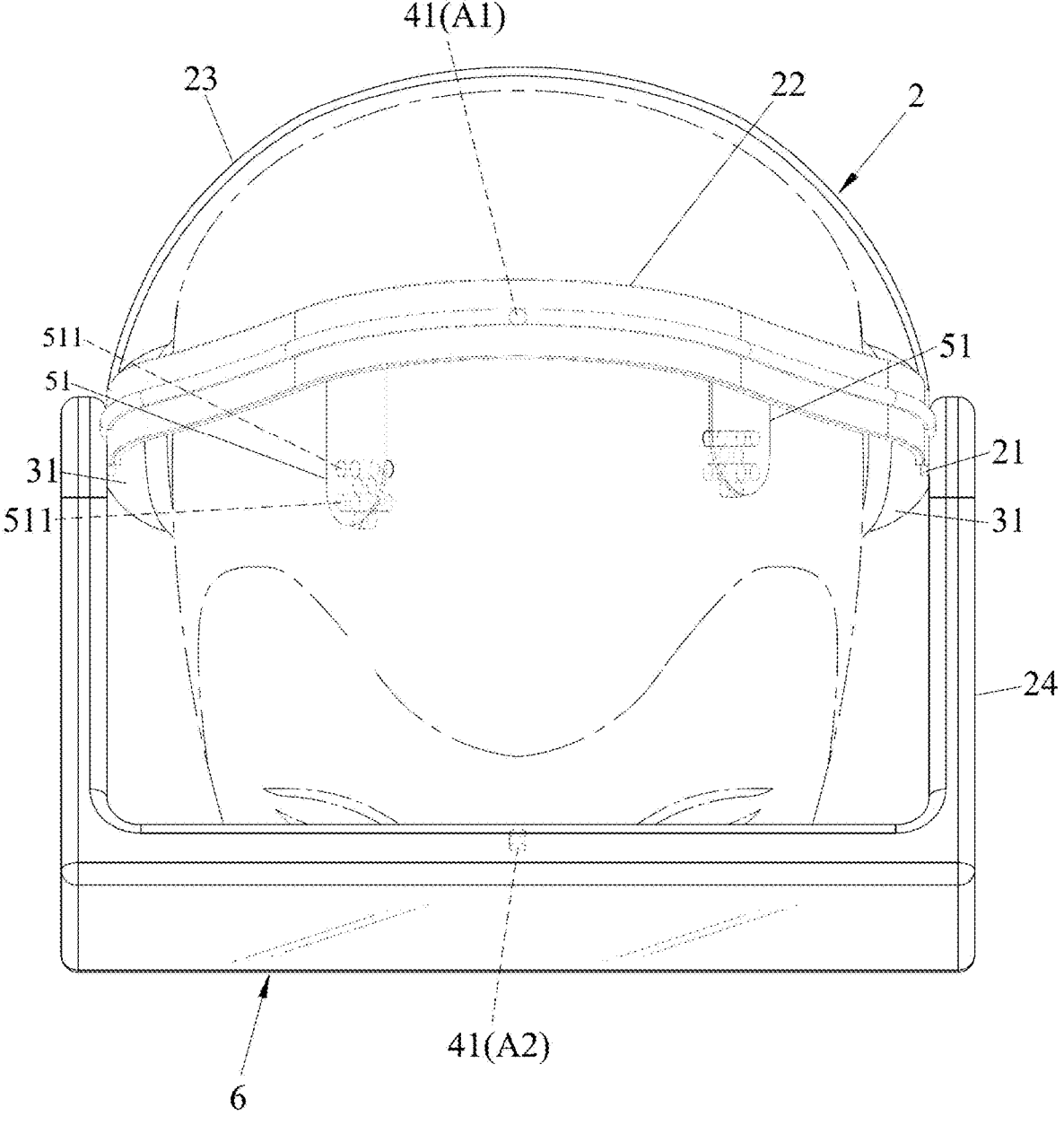
FIG. 5 is a fragmentary top view of the embodiment.

Referring to FIGS. 3, 4 and 5, the support unit 2 corresponds to a head shape of the user and comprising two ear portions 21 corresponding to both ears of the user 21, a top side portion 22 connected between the ear portions and upwardly crossing over the top of the head of the user, a rear side portion 23 connected between the ear portions 21 and rearwardly crossing over the rear skull of the user, and a front side portion 24 connected between the ear portions 21 and forwardly crossing over the user.

The audio stimulation unit 3 includes two speakers 31 arranged at the ear portions 21, the speakers 31 being used for broadcasting the binaural beats with frequency following response to two ears of the user, the binaural beats with frequency following response having an audio frequency difference. The binaural beats with frequency following response has an audio frequency difference between 0.1 Hz and 40 Hz. More specifically, the binaural beats with frequency following response has an audio frequency difference between 0.1 Hz and 12 Hz, and between 20 and 30 Hz.

With reference to FIGS. 1, 3 and 5, the acupoint stimulation unit 4 includes several acupoint agents 41, two gloves 42 and two foot covers 43. The acupoint agents 41 are correspondingly arranged on the support unit 2, the gloves 42 and the foot covers 43, and the acupoint agents 41 are used to output a laser light for physical stimulation of the user's acupoint. In the present embodiment, the laser light wavelength of the acupoint agents 41 is 500-900 nm, and the output power is 100-200 mW.

One of the acupoint agents 41 is adjustably provided at the center of the top side portion 22 to correspond to the Baihui acupoint (International acupoint code GV20) of the user, which is denoted by the reference numeral A1 in the drawings.

One of the acupoint agents 41 is adjustably provided at the front side portion 24 at a distance of ten times the finger distance from the center of the top side portion 22 forwardly to correspond to the Yintang acupoint of the user (International acupoint code EX-HN3), indicated by the reference numeral A2 in the drawings. In this embodiment, the finger distance is substantially 2.3 centimeters.

Two of the acupoint agents 41 are respectively provided at the foot covers 43 in an adjustable position and correspond to the Taichong acupoint (International acupoint code LR3) of the user, indicated by the reference numeral A3 in the drawings.

Two of the acupoint agents 41 are respectively provided on the gloves 42 in an adjustable position and correspond to the Hegu acupoint (International acupoint code LI4) of the user, indicated by the reference numeral A4 in the drawings.

It should be noted that, in the above-mentioned manner corresponding to the acupoint of the user, the electric resistance of the human skin can be measured near the acupoint, and the position of the acupoint can be taken as the position of the acupoint at the position with the lowest electric resistance. Then, the corresponding acupoint agents 41 can be adjusted to correspond to the position to complete the positioning of the acupoint.

The electronic stimulation unit 5 includes two electrical stimulation agents 51 arranged on the support unit 2, the electrical stimulation agents 51 being used for outputting physical stimulation to the head of the user. The electrical stimulation agents 51 are respectively arranged on the top side portion 22 to respectively correspond to an F3 position and an FP2 position in the international 10-20 system of electrode placement, wherein the electrical stimulation agents corresponding to the F3 position is used as a positive pole, and the electrical stimulation agents corresponding to the FP2 position is used as a negative pole.

In the present embodiment, the physical stimulation is a direct current for transcranial direct current stimulation (tDCS), the magnitude of the current is 0.5 mA-2 mA, and the current density is 0.03 mA/cm$^2$-0.09 mA/cm$^2$, but the present invention is not limited thereto. The physical stimulation can also be an electromagnetic pulse for transcranial magnetic stimulation (TMS), and the electromagnetic frequency is 1-20 Hz.

Each electrical stimulation agents 51 has several conductive posts 511 arranged in parallel to output physical stimulation.

Referring to FIGS. 1, 2 and 3, the display and optical frequency-flashed stimulation 6 is arranged on the support unit 2 and can switch between a display mode and an optical frequency-flashed stimulation mode, wherein the display and optical frequency-flashed stimulation 6 displays a virtual image for viewing by the two eyes of the user when in the display mode; and the display and optical frequency-flashed stimulation 6 stimulates the two eyes of the user with a flashing picture when in the optical frequency-flashed stimulation mode. In the present embodiment, the display and optical frequency-flashed stimulation 6 is a virtual image operation device, and includes a display module 61 and an operation button 62. The virtual image is a VR vision displayed by the display module 61.

When the display and optical frequency-flashed stimulation 6 is in the optical frequency-flashed stimulation mode, the flashing picture displayed by the display and optical frequency-flashed stimulation 6 flashes at a predetermined optical frequency, the predetermined optical frequency flash being between 45 Hz and 55 Hz. In other embodiments, when the display and optical frequency-flashed stimulation 6 is in the optical frequency stimulation-flashed mode, the flashing picture displayed by the display and optical frequency-flashed stimulation 6 respectively stimulates the two eyes of the user at an optical frequency-flashed difference.

The exercise unit 7 is operated by the user for taking exercise and includes a fitness bike 71 having a handle 711.

The measurement unit 8 includes a heart rate sensor 81 provided to the handle 711 for measuring the number of heart rates and a pulse wave of the user. In the present embodiment, the heart rate sensor 81 measures a minute electronic signal of the skin surface by an electrode when the human heart contracts, thereby measuring the heart rate number and the pulse wave. Since this technology is a prior technical means, the description will not further describe the principle.

The control unit 9 is electrically connected to the speakers 31, the acupoint agents 41, the electrical stimulation agents 51, the display and optical frequency-flashed stimulation 6, the exercise unit 7 and the measurement unit 8, stores digital information of the binaural beats with frequency following response, and can simultaneously control the speakers 31 to broadcast the binaural beats with frequency following response, the acupoint agents 41 to emit physical stimulation, the electrical stimulation agents 51 to emit physical stimulation, and the display and optical frequency-flashed stimulation 6 to switch between the display mode and the optical frequency stimulation-flashed mode according to a preset command. In the present embodiment, the control unit 9 is a personal computer. In the present embodiment, the digital information, the virtual image displayed by the display and optical frequency-flashed stimulation 6, and the default command are pre-stored in the control unit 9 after being downloaded via a cloud network 10.

Figure 6:
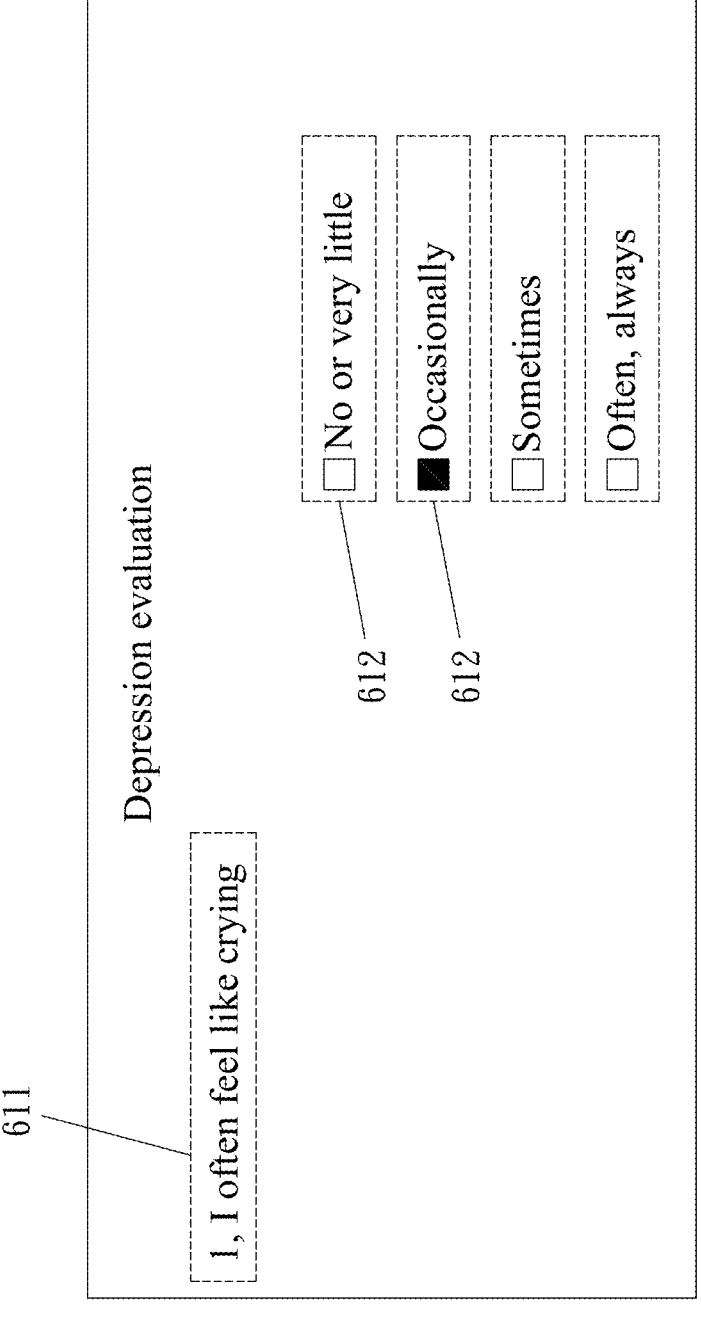
FIG. 6 is a schematic view of a picture displayed when an evaluation procedure is executed in the embodiment.

The control unit 9 is configured to perform a heart rate variation analysis based on the continuous pulse wave to derive a high frequency power parameter (High frequency power, HF, spectral range 0.15-0.4 Hz) which is displayed by the display module 61. It should be noted that the heart rate variation analysis (HRV) is a method for measuring the degree of continuous heart rate variation, and its calculation method mainly includes analyzing the time series of a heart beat and a heart beat interval obtained by electrocardiogram or pulse measurement. Since the heart rate variation analysis and obtaining the high frequency power parameter are common techniques for a person skilled in the relevant art, the description does not further describe the calculation method. Referring to FIGS. 2, 3 and 6, the control unit 9 can execute an evaluation procedure, the control unit 9 controls the display module 61 to sequentially display several self-assessment questions 611 for evaluating depression in the evaluation procedure, each self-assessment questions 611 having several self-assessment items 612, and the selected self-assessment items 612 can be changed by changing the direction of the display module 61; a depression self-assessment score corresponding to the selected self-assessment items 612 is generated for storage after confirmation via the operation button, and a depression result score is generated by summing all the depression self-assessment scores when all the depression self-assessment questions 611 have been answered. In the present embodiment, the display module 61 displays one set of depression self-assessment questions 611 at a time, and performs a next set of self-assessment questions 611 after the corresponding self-assessment items 612 have been selected, but this is not a limitation. In other embodiments, multiple sets of depression self-assessment questions 611 may be displayed at the same time, and the sources of the depression self-assessment questions 611 may be from the existing evaluation table as shown in FIG. 7, but this is not a limitation.

Referring to FIGS. 1, 2 and 3, the control unit 9 displays a prompt message in the virtual image by the display and optical frequency-flashed stimulation 6 in the display mode after the number of heart rates reaches a predetermined value for a predetermined time, and a prompt sound is produced by the speakers 31.

In use, the user first wears the support unit 2 on the head, and wears the gloves 42 and the foot covers 43, then rides on the fitness bike 71 and holds the handle 711 with both hands to perform riding movement. The gloves 42 is exposed from at least one hand's finger to contact the heart rate sensor 81, and then the control unit 9 controls the speakers 31 to broadcast the binaural beats with frequency following response, which causes the acupoint agents 41 to emit physical stimulation to the corresponding acupoint, and causes the electrical stimulation agents 51 to emit physical stimulation to the corresponding brain region. In this way, the user can receive the stimulation of the binaural beats with frequency following response, the acupoints and the brain regions at the same time, cooperate with the effect of the exercise, and further cooperate with the display and optical frequency-flashed stimulation 6 to display a comfortable vision in the display mode and with the display and optical frequency-flashed stimulation 6 to display a flashing picture in the optical frequency stimulation-flashed mode, thereby alleviating the symptoms of the patient with depression.

In addition, before use, the user may first perform an evaluation procedure to obtain a pre-operation depression result score, and then perform an evaluation procedure again to obtain a post-operation depression result score after the whole operation process is completed. The degree of depression improvement can be seen from the two depression result scores as a record and as a driving force for further use of the user.

In addition, the high frequency power parameter can be measured before the rehabilitation. In 10 minutes after the completion of the rehabilitation, the high frequency power parameter can be measured again, and the effect of the rehabilitation can also be known.

It is added that, in the present case, the test results corresponding to the effect of the physical stimulation of the acupoint agents 41 and the electrical stimulation agents 51 on the patient with depression have been proved by the following references. Therefore, no further explanation will be given in this description.

1. Liao Meili. (2001). Theoretical study of depression. Chinese Journal of Clinical Medicine of Traditional Chinese Medicine, 7(1), 31-35.
2. Lin Liqun. (2014). Acupuncture, alternative therapy for suicidal depression. Consultation and counselling, (346), 15-16.
3. Meron, D., Hedger, N., Garner, M., & Baldwin, D. S. (2015). Transcranial direct current stimulation (tDCS) in the treatment of depression: systematic review and meta-analysis of efficacy and tolerability. Neuroscience & Biobehavioral Reviews, 57, 46-62.
4. Brunoni, A. R., Moffa, A. H., Fregni, F., Palm, U., Padberg, F., Blumberger, D. M., . . . & Loo, C. K. (2016). Transcranial direct current stimulation for acute major depressive episodes: meta-analysis of individual patient data. The British Journal of Psychiatry, 208(6), 522-531.
5. Priori, A., Hallett, M., & Rothwell, J. C. (2009). Repetitive transcranial magnetic stimulation or transcranial direct current stimulation?. Brain stimulation, 2(4), 241-245.

In addition, the effect of exercise on the reduction of the melancholic state or the risk of developing depression has also been demonstrated by the following references.

6. Mead, G. E., Morley, W., Campbell, P., Greig, C. A., McMurdo, M., & Lawlor, D. A. (2008). Exercise for depression. Cochrane database of systematic reviews, (4).
7. Krogh, J., Hjorthøj, C., Speyer, H., Gluud, C., & Nordentoft, M. (2017). Exercise for patients with major depression: a systematic review with meta-analysis and trial sequential analysis. BMJ open, 7(9), e014820.
8. Beserra, A. H. N., Kameda, P., Deslandes, A. C., Schuch, F. B., Laks, J., & Moraes, H. S. D. (2018). Can physical exercise modulate cortisol level in subjects with depression? A systematic review and meta-analysis. Trends in psychiatry and psychotherapy, 40(4), 360-368.

Figure 8:
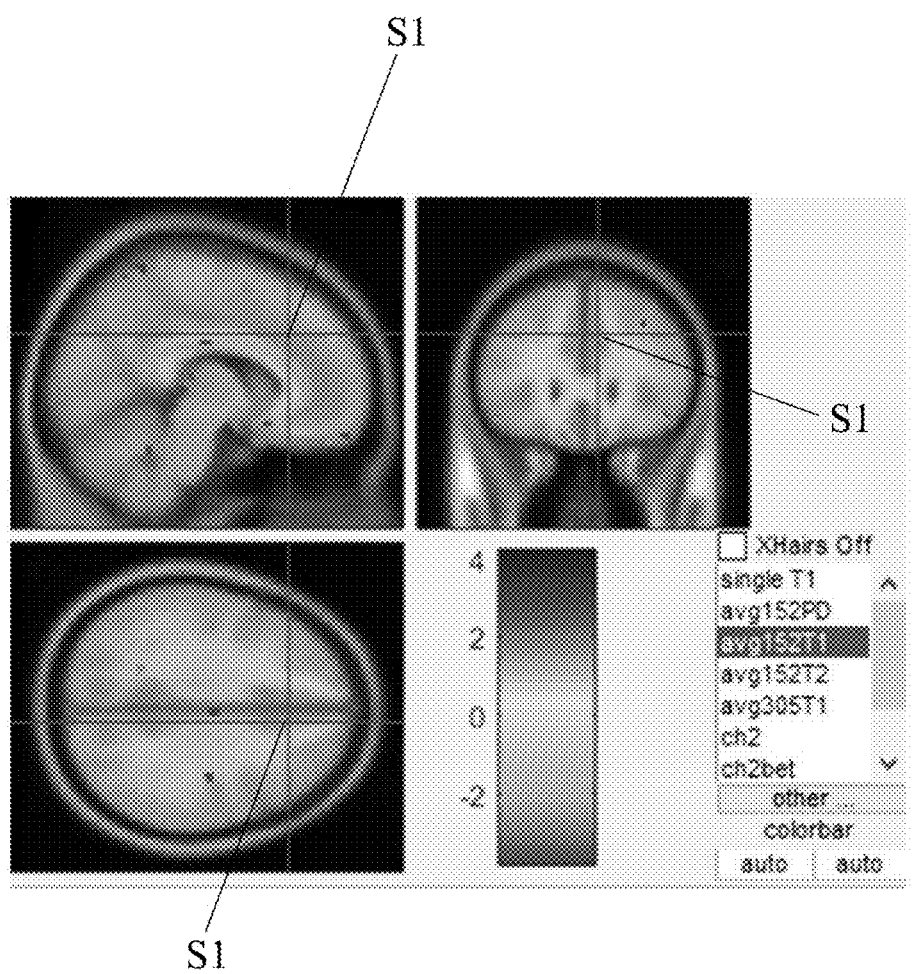
FIG. 8 is a three-dimensional magnetic resonance imaging vision of a subject listening to a binaural beats with frequency following response.
Figure 9:
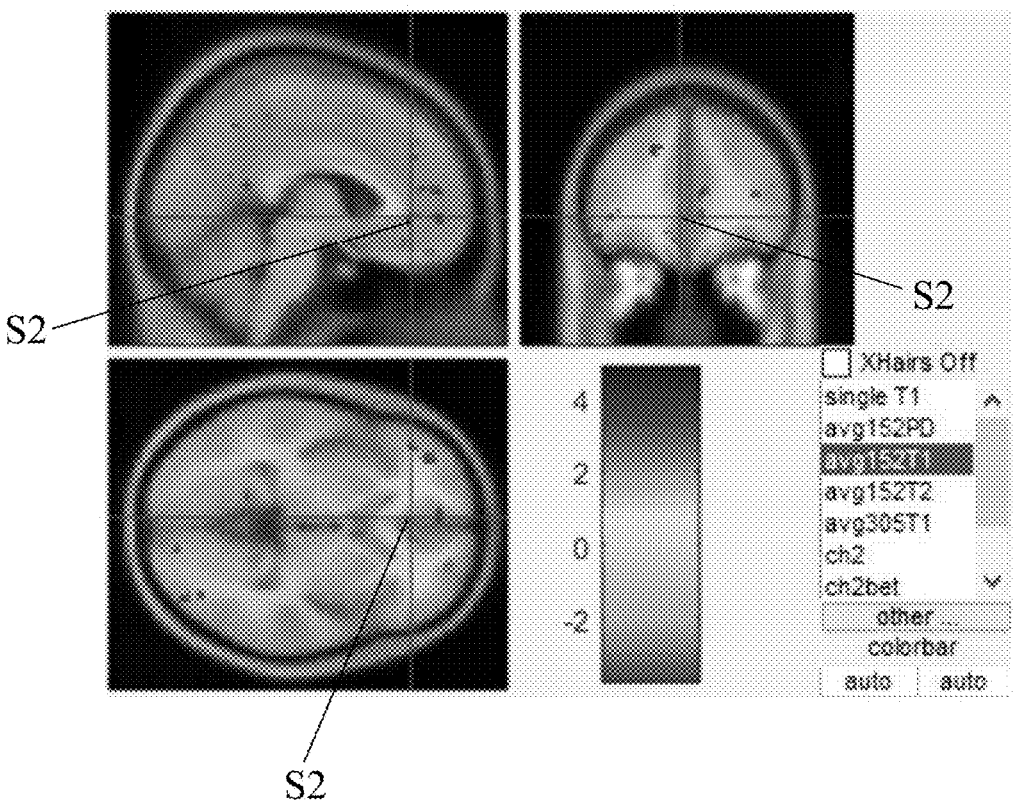
FIG. 9 is a three-dimensional magnetic resonance imaging vision of another subject listening to the binaural beats with frequency following response.

After further experimental verification by the applicant, with reference to FIG. 8, by taking a three-dimensional magnetic resonance imaging (MRI) vision of a subject listening to the binaural beats with frequency following response with an audio frequency difference of 20-24 Hz, it can be seen that activation occurs at the MRI brain positioning coordinate (8, 28, 34) (namely, a red activation region S1 at the blue cross in FIG. 8). With reference to FIG. 9, by taking a three-dimensional magnetic resonance imaging vision of another subject listening to the binaural beats with frequency following response with an audio frequency difference of 25-29 Hz, it can be seen that activation occurs at the MM brain location coordinate (−4, 38, −2) (i.e. a red activation region S2 at the blue cross in FIG. 9), demonstrating that listening to the binaural beats with frequency following response within this audio frequency difference range can have an effect on relevant brain regions of the patient with depression in the human brain. It is to be noted that the MRI brain positioning coordinate referred to can be judged by a person skilled in the relevant art according to the three-dimensional magnetic resonance imaging vision. Since it is not a main technical feature of the present case, the description will not be further described.

In addition, the experiment is performed by another healthy and voluntary female subject and another healthy and voluntary male subject. The female subject and the male subject both listen to an album with a 10 Hz difference in audio frequency of the binaural beats with frequency following response. However, the female subject in response to the binaural beats with frequency following response is increased from 3.96 pg/mL melatonin before listening to 4.84 pg/mL after listening, with a total increase of 0.88 pg/mL melatonin, while the male subject is increased from 3.14 pg/mL melatonin before listening to 3.78 pg/mL after listening, with a total increase of 0.64 pg/mL melatonin, thus demonstrating that the binaural beats with frequency following response in the low frequency band can increase melatonin and thus improve sleep, and adequate sleep can improve the symptoms of depression.

It is added that the heart rate variability analysis reflects a comprehensive indicator of the current physiological and psychological state of the subject and is an effective method in medicine to evaluate the function and balance of the autonomic nervous system (ANS). A typical heartbeat interval spectrum frequency occurs below 1 Hz, and a number of peaks can be found in the range of 0 to 0.4 Hz. It is mainly a high frequency region (0.15-0.40 Hz) and a low frequency region (0.04-0.15 Hz). The high-frequency region usually reflects the activity of parasympathetic nerve, while the low-frequency region is regulated by both sympathetic and parasympathetic nerve system. The high frequency power parameters show a significant downward trend in the heart rate variability analysis indicators in patients with depression. Therefore, if the depression symptoms can be improved, the high frequency power parameters will correspondingly increase.

In this study, seven subjects are tested. After listening for at least 20 minutes to the binaural beats with the audio frequency difference between 0.1 Hz and 12 Hz, the results shows that the high frequency power parameter corresponding to parasympathetic activity is increased by 4.5 n. u. while the heartbeat is decreased by 5 at rest, while the low-frequency power parameter corresponding to sympathetic activity is decreased by 3.5 n. u. which proves that the physical stimulation of the binaural beats with frequency difference may improve parasympathetic activity and reduce sympathetic activity.

Figure 10:
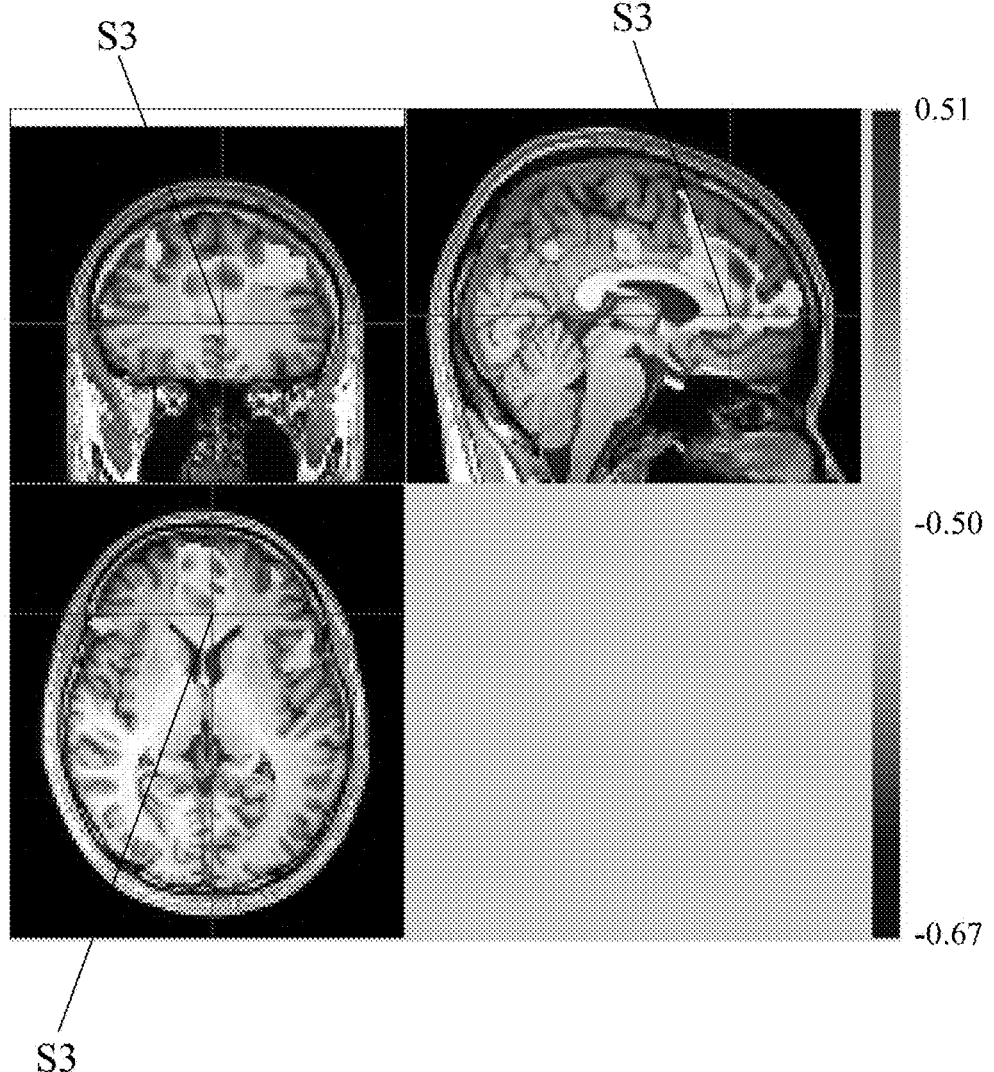
FIG. 10 is a magnetic resonance imaging vision of another subject after exposure to a predetermined optical frequency flash of 50 Hz, with the location shown indicating the left anterior cingulate cortex.
Figure 11:
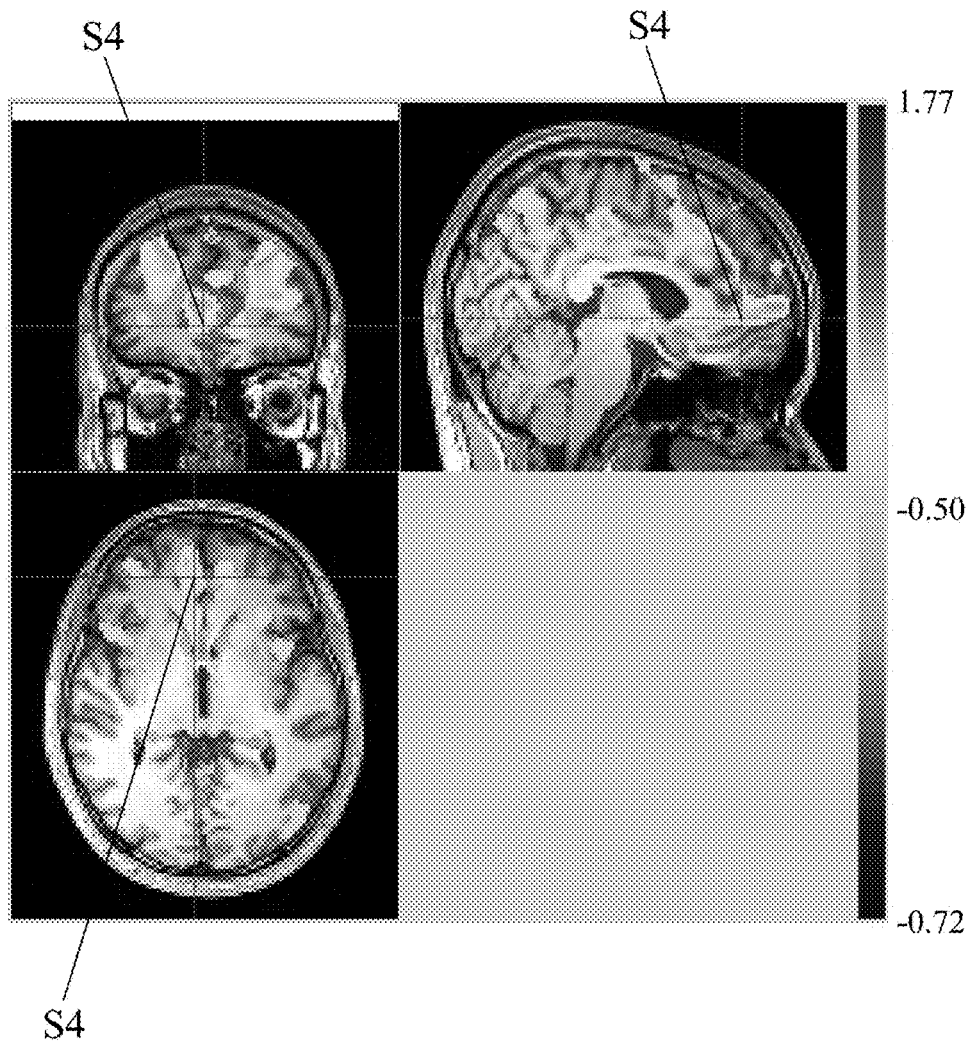
FIG. 11 is a vision similar to FIG. 10, with the location shown indicating the right anterior cingulate cortex.

With reference to FIGS. 10 and 11, the applicant has further experimentally verified that after the flicker light stimulation with the predetermined optical frequency flash of 50 Hz is performed on another subject, it can be seen that the MRI brain positioning coordinate (−2, 34, 4) of the left anterior cingulate cortex ACC (namely, the red activation region S3 at the red cross in FIG. 10) is activated, and the MRI brain positioning coordinate (6, 46, −2) of the right anterior cingulate cortex ACC (namely, a red activation region S4 at the red cross in FIG. 11) is activated, demonstrating that the optical frequency-flashed stimulation can affect relevant brain regions of the patient with depression in the human brain.

From the above description, it can be seen that the stimulation from the binaural beats with frequency following response, the acupoints, the brain regions and the movements, respectively, can change the activity phenomenon of the brain waves, dredge the meridians, promote the excitability of the cortical tissue and regulate the cortisol concentration, thereby alleviating the depression condition. The invention can enable the user to obtain multiple stimulation simultaneously in a single treatment course. Since it does not require each instrument to be performed in batches, the invention thus greatly reduces the rehabilitation time and improves the rehabilitation efficiency of the patient with depression.

In addition, since the physiological response of the human body will increase the production of melatonin in the period from the sunset to the evening, it can be seen that the audio frequency difference of the binaural beats with frequency following response is preferably between 0.1 Hz and 12 Hz when the rehabilitation assistant system is used by the patient with depression in the period from the sunset to the evening. In the daytime, the audio frequency difference of the binaural beats with frequency following response is preferably between 20 Hz and 30 Hz.

In addition, when performing the rehabilitation, the control unit 9 controls the display and optical frequency-flashed stimulation 6 to display the virtual image, so that the user can view the virtual image in the process of rehabilitation, so as to make the rehabilitation more enjoyable, thereby improving the user's willingness to perform rehabilitation. The user can learn the progress of the movement by displayed prompt messages and prompt sounds sent via the speakers 31, thereby improving the user's convenience.

In view of the above, by providing the speakers 31, the acupoint agents 41 and the electrical stimulation agents 51, the display and optical frequency-flashed stimulation 6 and the exercise unit 7, the user can simultaneously obtain multiple stimulation in a single treatment so as to improve the rehabilitation efficiency of the patient with depression, and thus can surely achieve the purpose of the present invention.

The above descriptions are merely embodiments of the present invention, which should not limit the scope of the present invention. All simple equivalent changes and modifications made according to the scope of the patent application of the present invention and the content of the patent description are still within the scope of the invention patent.

What is claimed is:

1. A rehabilitation assistant system for a patient with depression for use by a user, wherein the rehabilitation assistant system for the patient with depression comprises:

a support unit corresponding to a head shape of the user and comprising two ear portions corresponding to two ears of the user, a top side portion connected between the ear portions and upwardly crossing over the top of the head of the user, a rear side portion connected between the ear portions and rearwardly crossing over the rear skull of the user, and a front side portion connected between the ear portions and forwardly crossing over the user;

an audio stimulation unit comprising two speakers arranged at the ear portions, the speakers being used for broadcasting binaural beats to the two ears of the user, the binaural beats having an audio frequency difference in a range of 0.1 Hz-12 Hz or 20 Hz-30 Hz;

an acupoint stimulation unit comprising several acupoint agents, wherein at least a part of the acupoint agents are arranged on the support unit, the acupoint agents being used to output a laser light for physical stimulation of acupoints of the user; one of the acupoint agents is arranged at the center of the top side portion in an adjustable position so as to correspond to a Baihui acupoint of the user; one of the acupoint agents is arranged at the front side portion in an adjustable position and located forwardly at a distance of ten times a finger distance from the center of the top side portion so as to correspond to a Yintang acupoint of the user, the finger distance being approximately 2.3 centimeters;

an electronic stimulation unit comprising two electrical stimulation agents arranged on the support unit, wherein the electrical stimulation agents are used for either outputting a current to the head of the user to perform transcranial electrical stimulation or outputting an electromagnetic pulse to perform transcranial magnetic stimulation;

a display and optical frequency-flashed stimulation which is arranged on the support unit and can switch between a display mode and an optical frequency-flashed stimulation mode, wherein the display and optical frequency-flashed stimulation displays a virtual image for viewing by the two eyes of the user when in the display mode; the display and optical frequency-flashed stimulation stimulates the two eyes of the user with a flashing picture when in the optical frequency-flashed stimulation mode;

an exercise unit configured for being operated by the user to perform an exercise; and a control unit which is electrically connected to the speakers, the acupoint agents, the electrical stimulation agents, the display and optical frequency-flashed stimulation and the exercise unit, stores digital information about the binaural beats, and can simultaneously control the speakers to broadcast the binaural beats, the acupoint agents to emit physical stimulation, the electrical stimulation agents to emit physical stimulation, and the display and optical frequency-flashed stimulation to switch between the display mode and the optical frequency-flashed stimulation mode according to a preset command;

wherein one of the electrical stimulation agents corresponds to an F3 position in the international 10-20 system of electrode placement is used as a positive pole.

2. The rehabilitation assistant system for the patient with depression according to claim 1, wherein the laser light wavelength of the acupoint agents is 500 nm-900 nm, and an output power of the acupoint laser light is 3 joule-18 joule for each acupoint.

3. The rehabilitation assistant system for the patient with depression according to claim 1, wherein when the display and optical frequency-flashed stimulation is in the optical frequency-flashed stimulation mode, the flashing picture displayed by the display and optical frequency-flashed stimulation flashes at a predetermined optical frequency, the predetermined optical frequency being 45 Hz-55 Hz.

4. The rehabilitation assistant system for the patient with depression according to claim 1, wherein when the display and optical frequency-flashed stimulation is in the optical frequency-flashed stimulation mode, the flashing picture displayed by the display and optical frequency-flashed stimulation respectively stimulate the two eyes of the user with respective frequencies having an optical frequency-flashed difference.

5. The rehabilitation assistant system for the patient with depression according to claim 1, wherein the display and optical frequency-flashed stimulation is a virtual image operation device, and comprises a display module and an operation button; the control unit can execute an evaluation procedure, the control unit controls the display module to sequentially display several self-assessment questions for evaluating depression in the evaluation procedure, each self-assessment question having several self-assessment items, and the selected self-assessment items can be changed by changing the direction of the display module; a depression self-assessment score corresponding to the selected self-assessment items is generated for storage after confirmation via the operation button, and a depression result score is generated by summing all the depression self-assessment scores when all the depression self-assessment questions have been answered.

6. The rehabilitation assistant system for the patient with depression according to claim 1, wherein when the electrical stimulation agents are configured to output direct current, the current magnitude of the direct current is 0.5 mA-2 mA, and the current density of the direct current is 0.03 mA/cm2-0.09 mA/cm2; and when the electrical stimulation agents are configured to output an electromagnetic pulse, the electromagnetic frequency is 1-20 Hz.

7. The rehabilitation assistant system for the patient with depression according to claim 1, wherein the electrical stimulation agents are respectively arranged on the top side portion, one of the electrical stimulation agents is configured to correspond to an FP2 position in the international 10-20 system of electrode placement, and the one of the electrical stimulation agents corresponding to the FP2 position is used as a negative pole.

8. The rehabilitation assistant system for the patient with depression according to claim 7, wherein each of the electrical stimulation agents has several conductive posts arranged in parallel to output physical stimulation.

9. The rehabilitation assistant system for the patient with depression according to claim 1, further comprising a measurement unit including a heart rate sensor electrically connected to the control unit for measuring a heart rate of the user.

10. The rehabilitation assistant system for the patient with depression according to claim 9, wherein the control unit displays a prompt message in the virtual image by the display and optical frequency-flashed stimulation after the heart rate reaches a predetermined value for a predetermined time.

11. The rehabilitation assistant system for the patient with depression according to claim 9, wherein the heart rate sensor is further configured to measure a pulse wave, and the control unit is configured to perform a heart rate variability analysis based on successive pulse waves to derive a high frequency power parameter which is displayed by the display module.

12. The rehabilitation assistant system for the patient with depression according to claim 9, wherein the exercise unit comprises a fitness bike having a handle, and the heart rate sensor is disposed on the handle.

13. The rehabilitation assistant system for the patient with depression according to claim 1, wherein the acupoint stimulation unit further comprises two foot covers, two of the acupoint agents are respectively provided at the foot covers in adjustable positions and correspond to a Taichong acupoint of the user.

14. The rehabilitation assistant system for the patient with depression according to claim 1, wherein the acupoint stimulation unit further comprises two gloves, wherein two of the acupoint agents are respectively provided at the gloves in adjustable positions and correspond to a Hegu acupoint of the user.

15. The rehabilitation assistant system for the patient with depression according to claim 1, wherein the digital information, the virtual image and the preset command are pre-stored in the control unit after being downloaded via a cloud network.

\* \* \* \* \*